United States Patent [19]

Katinger

[11] Patent Number: 4,931,388

[45] Date of Patent: Jun. 5, 1990

[54] RETAINING BIOCATALYST PARTICLES IN A LIQUID MIXTURE

[76] Inventor: Hermann W. Katinger, Peter-Jordan-Str. 82, 1100 Vienna, Austria

[21] Appl. No.: 133,063

[22] PCT Filed: Mar. 3, 1987

[86] PCT No.: PCT/EP87/00125

§ 371 Date: Nov. 6, 1987

§ 102(e) Date: Nov. 6, 1987

[87] PCT Pub. No.: WO87/05322

PCT Pub. Date: Sep. 11, 1987

[30] Foreign Application Priority Data

Mar. 6, 1986 [AT] Austria .................................. 576/86

[51] Int. Cl.$^5$ ..................... C12P 1/00; C12N 11/00; C12N 5/02; C12M 1/40
[52] U.S. Cl. ..................................... 435/41; 435/174; 435/240.23; 435/240.25; 435/240.46; 435/261; 435/286; 435/288; 435/313; 435/315; 435/813; 435/818; 210/780
[58] Field of Search ..................... 435/41, 174, 240.21, 435/240.25, 240.46, 261, 284, 286, 288, 313, 315, 813, 818; 210/780

[56] References Cited

U.S. PATENT DOCUMENTS

| 3,263,817 | 8/1966 | Buckley | 210/388 |
|---|---|---|---|
| 3,766,059 | 10/1973 | Sasaki | 210/748 |
| 3,870,640 | 3/1975 | Reece et al. | 210/388 |
| 4,251,633 | 2/1981 | Orlowski et al. | 435/288 |
| 4,259,449 | 3/1981 | Katinger | 435/240.25 |
| 4,535,062 | 8/1985 | Muller | 435/315 X |
| 4,659,662 | 4/1987 | Hsu | 435/288 X |
| 4,828,719 | 5/1989 | Katinger | 210/780 |

*Primary Examiner*—David M. Maff
*Attorney, Agent, or Firm*—Michael J. Striker

[57] ABSTRACT

Biocatalyst particles of a predetermined size are retained in a liquid mixture by oscillating in a vertical direction a screen having openings with a passage width greater than the size of the biocatalyst particles. Preferably the screen is substantially cylindrical having an interior that encloses a liquid column in a container which may be substantially cylindrical. Gas may be introduced into the liquid column and mixing means can be used to create flow currents on either or both sides of the screen. The mixing means may be a plurality of perforated discs connecting the screen to a centric gas delivery pipe in the column. Oscillating of the screen may be at a frequency between 10 and 100 Hertz and an amplitude between 0.5 to 50 times the biocatalyst particle size. Changing the frequency and amplitude varies retaining action of the screen.

12 Claims, 3 Drawing Sheets

RETAINING BIOCATALYST PARTICLES IN A LIQUID MIXTURE

The invention is directed to a method for treating a liquid mixture containing biocatalysts or comparable particles, in which liquid from the mixture is allowed to pass through an oscillated screen surface while particles are retained, and to a corresponding device comprising a container for receiving the mixture, a screen device for removing liquid from the mixture, which screen device admits this mixture during operation and retains particles of a predetermined minimum size; it is also directed to possible devices for introducing gas and/or nutrients or for the drainage of the liquid which has passed through the screen device.

It is known to immobilize biocatalysts, such as microorganisms, cell cultures, carriers or similar particles with or without bound, biologically active substances, etc., against flushing by means of mechanical mechanisms, such as screens, whose openings have passage widths which are narrower them to the size of the particle to be retained, or by means of attaching the biocatalysts to installations or carrier particles which are static or suspended in the liquid, or by means of the inclusion of the cells in gels such as alginates or the like, or also by means of sedimentation. However, all of the methods mentioned have considerable disadvantages in practice. For example, screens have a strong tendency to shift, since the particles are forced into the through-openings of the screen because of the liquid currents, and these through-openings are therefore opened from time to time, and the particles must be put in suspension again. Also, it is possible to cancel the retaining action only by means of special steps, such as removing the screen or flushing at a high through-flow rate. When biocatalysts are attached to packing bodies or installations, the culture is very sensitive, since an operation diverging from the ideal conditions often causes the biocatalysts to fall off. Moreover, the portion of the biocatalysts needed for the attachment is blocked for the reaction. The same applies for biocatalysts included in gels or the like, in which diffusion barriers occur and particles which are no longer effective biologically remain in the reaction space as ballast. The biocatalysts, as such, are therefore often kept in suspension in the reaction vessel, wherein the particles which are flushed from the reaction vessel in the course of obtaining the reaction product are mechanically separated from the liquid, for example, by means of separation, sedimentation or the like.

In addition, a method and a device for classifying solids suspended in liquids are known from Swiss Patent No. CH-PS-602 102, in which the mixture is fed to an oscillated screen basket through which the liquid and the desired small particles pass, while the particles which do not pass through the screen opening are retained, but the vibration prevents a filter cake from being built up. However, this procedure does not concern the retention of particles which are smaller than the screen openings.

SUMMARY OF THE INVENTION

It is the object of the invention to provide a method and a device for treating a liquid mixture containing biocatalysts or similar particles of the type mentioned in the beginning, which enables the biocatalysts and similar particles to be retained to the greatest extent in a simple manner such that the retention is easy to control and cancel.

In order to meet this object, the method, according to the invention, is characterized in that a filter surface comprising openings which are passable for the particles to be retained is oscillated in such a way as to impede the passage of these particles at least to a great extent.

The oscillations of the screen surface produce pressure waves in the liquid mixture, which pressure waves substantially prevent the biocatalysts and/or similar particles from passing through the screen openings, which are larger in comparison, and simultaneously suppress a plugging up of the openings by means of the formation of bridges. On the other hand, biologically inactive particles, which have crumbled into small fragments, can pass through the screen openings. In order to cancel the retaining action one need only terminate the vibration of the screen surface or correspondingly alter its amplitude and/or frequency.

The device according to the invention allows the retaining action to be adjusted to the respective desired value and also allows the frequency and/or amplitude of the oscillations to be changed at any time during the operation in an expedient manner by means of corresponding regulation of the oscillations produced by means of the vibration device. Since biocatalysts, in contrast to packing particles or carrier particles, can frequently be deformed to a limited degree, special retaining effects can be achieved by means of expedient adjustment of the frequency and amplitude of the oscillations, while taking into account the flow rate of the liquid through the screen openings. Since there are no rotating parts in the device according to the invention, a long-term extended operation under sterile conditions is easily possible.

If the filter member, which is preferably substantially cylindrical, reaches downward until close to the base of the container and comprises in its interior a gas feed pipe reaching until close to the lower end of the screen member, the liquid column enclosed by the screen member can be effectively enriched with gas. The vertical vibration of the screen member produces corresponding currents in the liquid which fills its interior; these currents promote a distribution of the gas in the liquid so that a gassing is achieved which is extensively free of bubbles. This is an important advantage, since gas bubbles are harmful to many reactions because defective reactions can result in the foam space. The liquid, which is saturated with dissolved gas, in the interior of the vibrating screen member can diffuse outwardly through the screen member into the reaction space containing the biocatalysts to be retained, so that no gas bubbles can occur there and an expensive permeation gassing by means of permeation tubes placed in the reaction chamber can be dispensed with.

In order to achieve a particularly good gas saturation in the interior of the cylindrical screen member the latter can be connected with a centric gas delivery pipe by means of one or more perforated disks, known per se, each of which comprises a plurality of perforations which narrow continuously in an upward or downward direction. Such perforated disks, or the like mixing devices, can also advisably project radially outward over the screen member and can also be provided with corresponding perforations in this area, which ensures a thorough mixing of the gas-saturated liquid, which has diffused through the screen member into the reaction space, with the mixture located in this place and, moreover, contributes in suppressing a shifting of the screen openings by means of the particles to be retained. Since the liquid is substantially not compressible, an acceleration of the liquid currents which are pressed through the perforations occurs during the vibration of the perforated disks connected with the screen member as a result of the conical construction of the perforations; this acceleration results in an intensive blending and an increased interphase exchange of gas and liquid, so that the gas exiting from the gas delivery pipe is quickly dissolved and a saturation of the liquid with dissolved gas is achieved. If additional backflow openings are arranged in the perforated disks in the vicinity of the screen member, this action is further improved.

In order that the device can also be operated with an alternating liquid state, the gas delivery pipe can be used alternately for delivering the gas or removing the liquid by means of suitable reversing valves.

A preferred embodiment form of the device, according to the invention, will be explained in more detail in the following by means of the attached drawings.

DETAILED DESCRIPTION OF THE PREFERRED EMBODIMENTS

Figure 1:
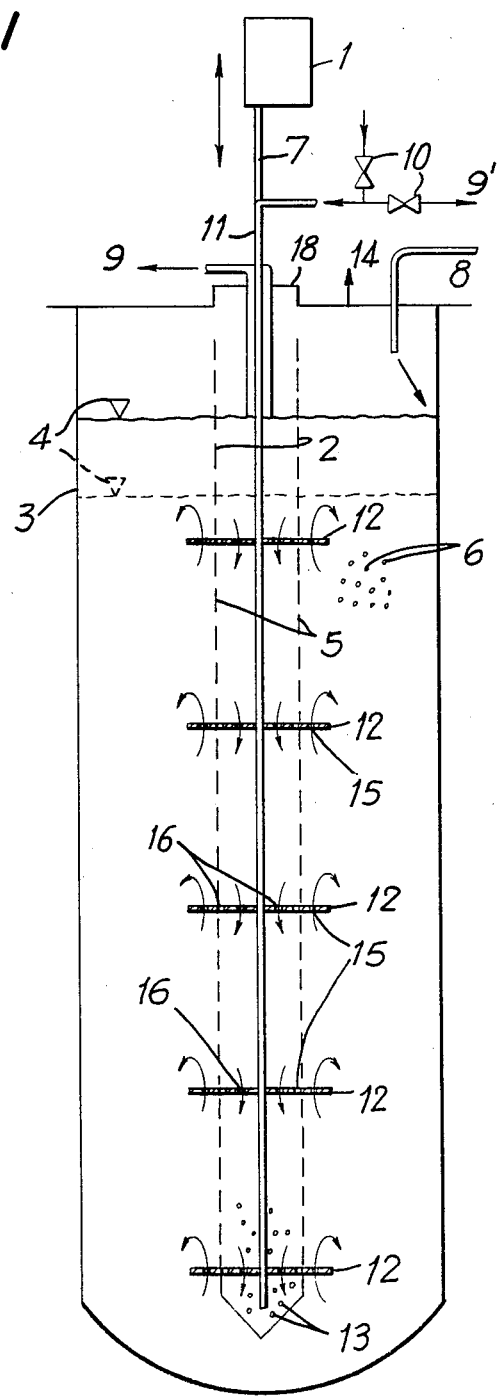
FIG. 1 schematically shows a vertical section through the device.

The device which is shown schematically in FIG. 1 comprises a substantially cylindrical container 3 which is tightly closed by a cover and has a curved base and a retaining device 2 which extends coaxially through a central opening of the cover into the container 3 until close to the base of the latter and comprises a cylindrical screen or filter member 5 which is concentric to the peripheral wall of the container 3 and is connected with a central gas delivery pipe 11 by means of a plurality of perforated disks 12 for a joint movement therewith. The vertical gas delivery pipe 11 is connected with a controllable vibration device 1 via a shaft 7; by means of this vibration device 1 the entire retaining device 2 can be oscillated via the shaft 7 and the gas delivery pipe 11 in a vertical direction. The amplitude and/or frequency of the oscillations can be adjusted in the vibration device 1. The part of the gas delivery pipe 11 which penetrates the cover is enclosed by a discharge pipe 9 whose lower end ends at the maximum filling level 4 of the container 3. The annular space between the discharge pipe 9 and the circumferential rim of the central opening of the cover is hermetically sealed by means of an oscillating diaphragm 18.

The container 3 is filled up to the filling level 4 with a liquid mixture containing biocatalysts 6 in suspension. Other liquid mixture or auxiliary materials required for the intended biological reactions, for example, a nutritive medium, can be fed via a delivery pipe 8 which is arranged in the cover and can be blocked. The screen or filter member 5 has a screen surface with a plurality of uniform openings whose clear passage width is dimensioned so as to be sufficiently larger than the particle size of the biocatalyst particles 6. The screen surface has an input side which contacts the liquid mixture and an output side opposite to the input side and which defines an inner space of the screen member. Therefore when the screen member 5 is stopped, these particles can pass through the screen openings. However, during operation, the screen member 5 is oscillated by means of the vibration device 1, the frequency and amplitude of the oscillations being adjusted to one another, while taking into account the speed at which the liquid flows through the screen openings. The screen member 5 is oscillated in such a way that the biocatalyst particles 6 to be retained are substantially completely prevented from passing through the screen openings. In addition, during operation, a suitable gas or gas mixture is advisably introduced by means of a reversing valve 10 and the gas delivery pipe 11 into the lowest part of the liquid column enclosed by the cylindrical screen member 5 in the retaining device 2. By means of the vibration of the screen member 5 and the perforated disks 12, the fine gas bubbles exiting from the lower end of the gas delivery pipe 11 in the surrounding, intensively mixed liquid are brought into contact with continuously new liquid which is ready to absorb, so that the gas components required for the intended reaction are dissolved in the surrounding liquid. Since the gas bubbles 13 cannot pass through the screen openings of the screen member 5, which are only approximately 10 to 100 ↑ m, but since, on the other hand, the liquid which is enriched or saturated with the dissolved gas components can easily diffuse through the screen openings, a rapid and good distribution of the liquid, which is enriched with the gas components, is also achieved in the reaction space surrounding the cylindrical screen member 5 by means of the vibration of the retaining device 1 and the pump action connected with it. Since this is also mixed simultaneously with the liquid which is fed via the delivery pipe 8, very favorable reaction conditions for the cultivation of the biocatalyst particles or the sought for reactions, respectively, result with substantially complete retention of the biocatalyst particles 6.

If the container 3 is filled up to the filling level 4, excess liquid can be drawn off via the discharge pipe 9 in order to prevent the filling level from rising further. Insofar as valuable substances are formed in the liquid during the cultivation which is carried out in the container 3, which valuable substances are soluble or flow away through the screen openings of the screen member 5, the latter can be guided off and obtained together with the liquid via the discharge pipe 9. During an operation of the device with only partial filling or an alternating filling level, the liquid which is enriched with valuable substances can also be guided away into another discharge line 9' via the gas delivery pipe 11 and a further reversing valve 10.

Figure 2:
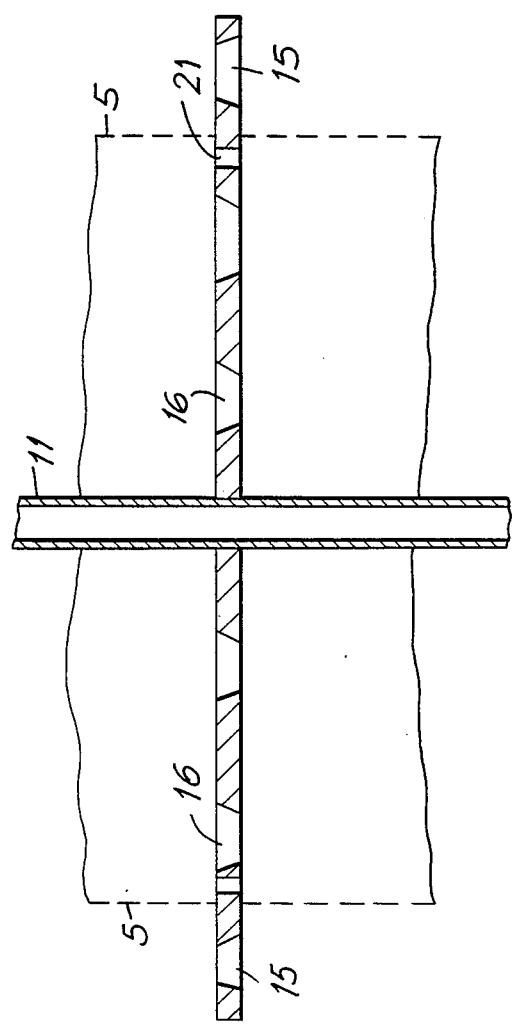
FIG. 2 shows a cross-section of a perforated disk connecting the filter member with the gas delivery pipe.

The perforated disk 12, which is shown schematically in FIG. 2, is connected with the central gas delivery pipe 11, on the one hand, and with the screen member 5, on the other hand, so as to execute a joint movement and comprises a plurality of through-openings 16 in its area enclosed by the screen member 5, which through-openings 16 taper conically in a downward direction, as well as additional backflow openings 21 in the vicinity of the screen surface of screen member 5, and through which the liquid flows in a direction opposite to the direction in which the liquid flows through openings 16. In addition, through-openings 15, which taper conically in an upward direction, are arranged in the outer rim of the perforated disks 12 which rim projects radially outwards over the screen member 5. If the retaining device 2 is made to execute vertical oscillations by means of the vibration device 1, the conical through-openings 15 and 16 produce liquid flows with corresponding pump action, which liquid flows are indicated by means of the arrows in FIG. 1. Instead of the perforated disks 12 shown in FIG. 2, one can also use disks having a cross-sectional area of opening which is reduced continuously in a different manner in a downward or upward direction or comprising other mixing elements for the production of liquid flows which promote thorough mixing. Gas bubbles 13 are constantly circulated in the interior of the screen member 5 by means of the pump action of the through-openings 16 and are absorb, without them coming into contact with the brought into contact with new liquid, which is ready to biocatalysts retained outside the screen member 5.

Since it is substantial to the invention that the screen openings of the screen member 5 clearly have a larger relative clear passage width than the particle size of the particles to be retained and the retaining action is accordingly determined in a decisive manner by means of the adjusted frequency and amplitude of the vibration, their retention can be canceled simply by means of stopping the vibration or by means of suitable reduction of its frequency and/or amplitude, or it can be limited to any desired value.

EXAMPLE 1

In a vibration fermenter (CHEMAP LF) similar to the device shown in FIG. 1, comprising an approximately 30 cm high cylindrical container (working volume 7 l) with a curved base and a base stirrer (diameter 10 cm), a retaining device connected with a vibration mixer was centrally arranged with a vertical cylindrical screen member (diameter 3 cm, height 18 cm; stainless steel screen, square mesh woven fabric with screen opening of 80 $\mu$m). The screen member was connected with a gas delivery pipe by means of four perforated disks (spacing 5 cm) so as to perform a joint vibrating motion, the gas delivery pipe being fastened to the vibration mixer and projecting into the container through a central opening.

Figure 3:
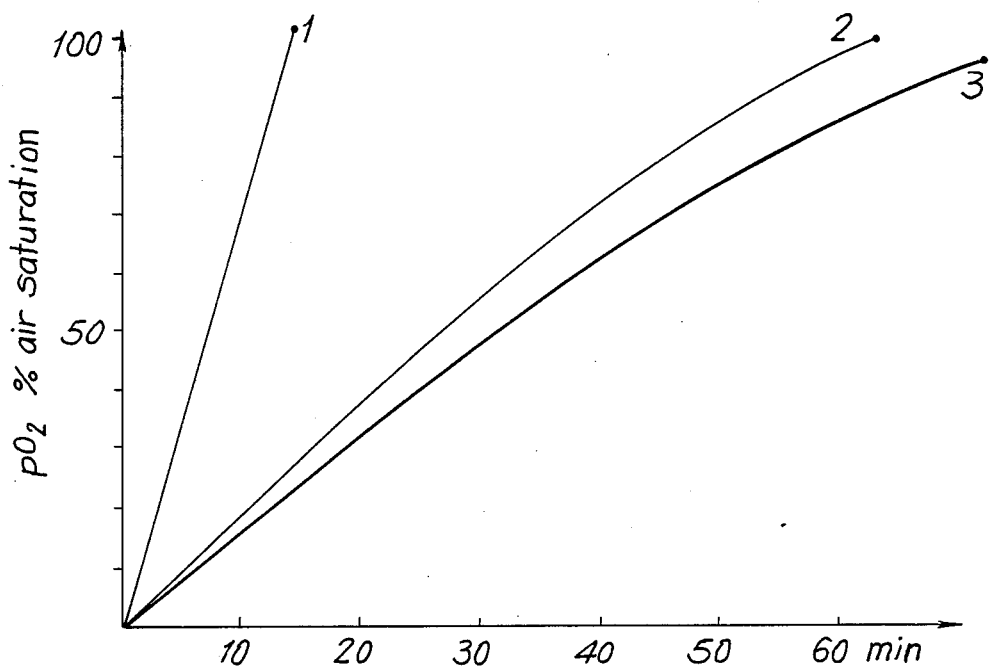
FIG. 3 shows a graphic illustration of the aeration achieved in such a device.

The container was filled with 7 l of water and its temperature was adjusted to 37° C. A $pO_2$ probe projecting into the container was calibrated in such a way that a value of 100% was indicated at a stirring speed of 30 r.p.m. of the base stirrer (not shown) and saturation with air on the oxygen scale. In order to determine the aeration capacity, the oxygen partial pressure was first lowered toward 0% by means of gassing with nitrogen accompanied by vibration of the screen member and then gassing was carried out with air and pure oxygen under various operating conditions via the interior of the screen member in such a way that the gas phase is dispersed only in the inner space enclosed by the screen member, and the gas arrives in the surrounding container space through the screen only in dissolved form. The results of this test are shown in FIG. 3. The curve 1 was obtained when introducing 7 l/h $O_2$ with an amplitude of approximately 2 mm and the curves 2 and 3 when introducing 7 l/h air at an amplitude of approximately 2 mm or approximately 0.8 mm.

EXAMPLE 2

The vibration fermenter used according to example 1 was provided with an oxygen regulating device which automatically shuts off the gas feed when a predetermined oxygen partial pressure is reached and additionally reduces the amplitude of the vibration mixer to an adjustable minimum value. As soon as the predetermined oxygen partial pressure is fallen short of because of the oxygen consumption, the regulating device automatically opens the gas feed (oxygen or air) and increases the amplitude of the vibration mixer again to the higher value. The higher amplitude, which serves to intensify the aeration, and the lower amplitude, which contributes only to keeping the screen surface free of particles, can be preselected as desired.

In the vibration fermenter, which is equipped in this way, mammal cells were cultivated in a cultivation test on a microcarrier (Cytodex 3 of the Pharmacia company, Uppsala). The conditioning of the microcarriers, the preliminary treatment of the cell inoculum and the cell count are effected according to the standard methods published by the Pharmacia company. During the test, a temperature of 37° C. was maintained in the fermenter and a pH value of 7.2 was maintained in the aeration gas by means of the addition of $CO_2$. The stirrer speed was 30 r.p.m. and the oxygen partial pressure corresponded to 20% air saturation ($pO_2$ set point). The vibration mixer was adjusted to a higher amplitude of approximately 1.2 mm and a lower amplitude of approximately 0.5 mm. For aeration, 200 ml of air per minute, with $CO_2$ automatically mixed in via the pH regulator, and 100 ml of oxygen per minute, via the screen member after each automatic regulation by means of the oxygen regulating device, are introduced into the head space of the container.

Figure 4:
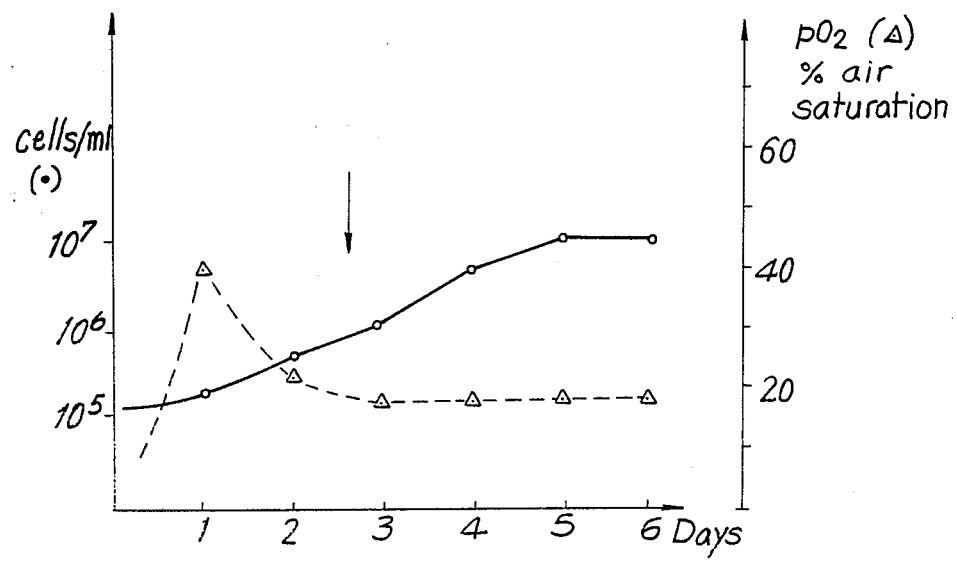
FIG. 4 shows a graphic illustration of the results of a cultivation of mammal cells on a microcarrier

In order to prepare the inoculum, cells of the Mouse L cell line in roller flasks in DMEM (GIBCO)+10% fetal calve's serum (FCS) is preferred, dissolved by trypsinization after 5 days according to established test protocol, and added to presterilized Cytodex 3 microcarriers conditioned in DMEM according to established protocol of the company Pharmacia, Uppsala. The inoculum density was selected after counting in a Thoma chamber (hemacytometer) in such a way that 35 g of microcarrier are mixed in 2.5 liters nutritive solution (DMEM+10% FCS) with approximately $7-8 \times 10^8$ cells and transferred to the presterilized fermenter immediately after mixing. For the purpose of colonization, the microcarrier, with cells, was stirred for a period of 4 hours in 1-2 minute cycles at 30-40 r.p.m. and the stirrer is stopped approximately 30 minutes afterward. This procedure was repeated eight times. The stirrer was then set at a speed of 30 r.p.m., the container was gradually filled (over approximately 2 hours) with nutritive solution (DMEM+10% FCS) to a final volume of 7 liters, the head space was gassed with a gas mixture (air+$CO_2$) and the culture was left standing after adjusting the aforementioned set points. A specimen was drawn once daily and the cell count determined according to established methods. Two days after the beginning of the culture, 3 liters of fresh nutritive solution per day was added via a feed in the cover of the fermenter with a dosing pump and excess culture was drawn off via the level pipe within the screen member together with gas phase. The test results shown in FIG. 4 show that the aeration capacity from the head space of the container was no longer sufficient after approximately two days. The place marked with the arrow shows the beginning of the automatic aeration via the screen member.

I claim:

1. A method of treating a liquid mixture containing biocatalyst particles of a predetermined size, the method comprising the steps of:
- providing a screen member having a substantially cylindrical screen surface for passing a liquid therethrough in a container containing the liquid mixture, said screen member having an input side for contact with the liquid mixture and an output side defining an inner space of said screen member, the inner space of said screen member defining a column enclosing a portion of said liquid mixture in the container and said screen surface including openings having a passagewidth which is greater than the predetermined size of the biocatalyst particles;
- oscillating the screen member in a vertical direction to prevent passage of said particles through the openings therein;
- introducing gas into the liquid column enclosed by the screen member on the output side of the screen member; and
- providing flow currents to enable mixing the liquid on at least one of the input and output sides of the screen member.

2. A method according to claim 1, wherein said screen surface has openings with a passage width which is 10 to 15 percent greater than the size of the biocatalyst particles, said oscillating step includes oscillating the screen surface at a frequency between 10 and 100 Hertz, which frequency is adapted to a flow rate with which the liquid passes through the screen surface, and an amplitude between 0.5 and 50 times the biocatalyst particle predetermined size.

3. A method according to claim 1, comprising the step of regulating introduction of the gas and a frequency and amplitude of oscillation in such a way that liquid enriched with a dissolved gas diffuses through the screen surface into the mixture containing the biocatalyst particles.

4. A method according to claim 1, wherein said oscillating step includes changing at least one of frequency and amplitude of oscillation of said screen surface to change a retaining action of the screen surface.

5. A device for treating a liquid mixture containing biocatalyst particles of a predetermined size, the device comprising:
- a screen member having a substantially cylindrical screen surface for passing a liquid therethrough in a container having an interior for containing the liquid mixture, said screen member having an input side for contact with the liquid mixture, and an output side defining an inner space of said screen member, the inner space of said screen member defining a column in the container for enclosing a portion of the liquid mixture to be treated in the container, and said screen surface including openings having a passage width greater than the predetermined size of the biocatalyst particles;
- means for oscillating said screen member in a vertical direction to prevent passage of the biocatalyst particles through said openings in said screen surface;
- means for introducing gas into said inner space on the output side of said screen member; and
- means for producing flow currents to enable mixing in the liquid and connected with said screen member.

6. A device according to claim 5, further comprising, means for communicating the interior of said container with a source of the liquid mixture, and said screen member having an end located adjacent to said base.

7. A device according to claim 5, wherein said screen member has a lower end, said gas introducing means including a gas delivery pipe connected with said oscillating means and extending into said screen member centrally thereof, said gas delivery pipe having an end located adjacent to said lower end of said screen member.

8. A device according to claim 5, wherein said mixing means includes at least one perforated disc which connects said screen member with said gas delivery pipe.

9. A device according to claim 8, wherein said mixing means includes a plurality of perforated discs, each of said plurality of perforated disc comprising through openings tapering continuously at least in one of downward and upward directions.

10. A device according to claim 9, wherein each of said perforated discs includes additional backflow openings within said inner space of said screen member.

11. A device according to claim 10, wherein said container has an uppermost filling level, said device further comprising a discharge pipe extending from said uppermost filling level of said container.

12. A device according to claim 11, wherein said gas delivery pipe includes a reversing valve and is used for drawing off a liquid.

* * * * *